United States Patent [19]

Moore et al.

[11] Patent Number: 4,755,610

[45] Date of Patent: Jul. 5, 1988

[54] HAPALINDOLES

[75] Inventors: Richard E. Moore; Gregory M. L. Patterson, both of Honolulu, Hi.

[73] Assignee: University of Hawaii, Honolulu, Hi.

[21] Appl. No.: 829,632

[22] Filed: Feb. 14, 1986

Related U.S. Application Data

[63] Continuation of Ser. No. 648,114, Sep. 7, 1984, abandoned, which is a continuation-in-part of Ser. No. 638,847, Aug. 8, 1984, abandoned.

[51] Int. Cl.$^4$ .................. C07D 209/90; C07D 209/18
[52] U.S. Cl. ................................. 548/425; 435/121; 435/257; 548/511
[58] Field of Search ............................... 548/425, 511

[56] References Cited

PUBLICATIONS

Biol. Abstr. 51:45694, abstracting O. P. Sachkova et al., "Problem on the Interspecies Antagonism of Cyanophyta Representatives," Vestn. Akad. nauk Kazakn. S.S.R. 25(5) 69–71.
M. R. Hagadone et al., "Defense Allomones of the Nudibranch Phyllidia *varicosa* Lamarck 1801," *Helv. Chim. Acta* 62(7) 2484–2494 (1979).
M. Nobuhara et al., "A Fungal Metabolite, Novel Isocyano Epoxide," *Chem. Pharm. Bull* 24(4), 832–834 (1976).
H. Achenbach et al., "Zur Biogenese des Xanthocillins," *Z. Naturforsch B.* 20, 137 (1965).
*Chem. Abstr.:* 6362c (1958), abstracting I. Hagedorn et al., "Clarifying the Constitution of Xanthocillin," *Pharmazie* 12, 567–580 (1957).
D. Brewer et al., "Isonitrile Acids from Cultures of the Fungus *Trichoderma hamatum* (Bon.) Bain. aggr., X-Ray Structure," *J.C.S. Chem. Comm.* 1979, 1061–1062.
J. Tsaklidis et al., Chem. Abstr. 87:84758k (1977).
P. N. Srivastava, "Taxonomy and Biology of Blue–Green Alga" T. V. Desikachary, ed., U. Madras, 1972, pp. 391–392.
R. Moore et al, J. Am. Chem. Soc. (1984), 106, 6456–6457.

*Primary Examiner*—Mary E. Ceperley
*Attorney, Agent, or Firm*—Nancy J. Harrison; Leroy Whitaker

[57] ABSTRACT

New alkaloids called hapalindoles, which are antibacterial and antifungal agents, and methods of preparing these alkaloids by culturing the blue-green alga *Hapalosiphon fontinalis* ATCC 39694, are provided.

8 Claims, 1 Drawing Sheet

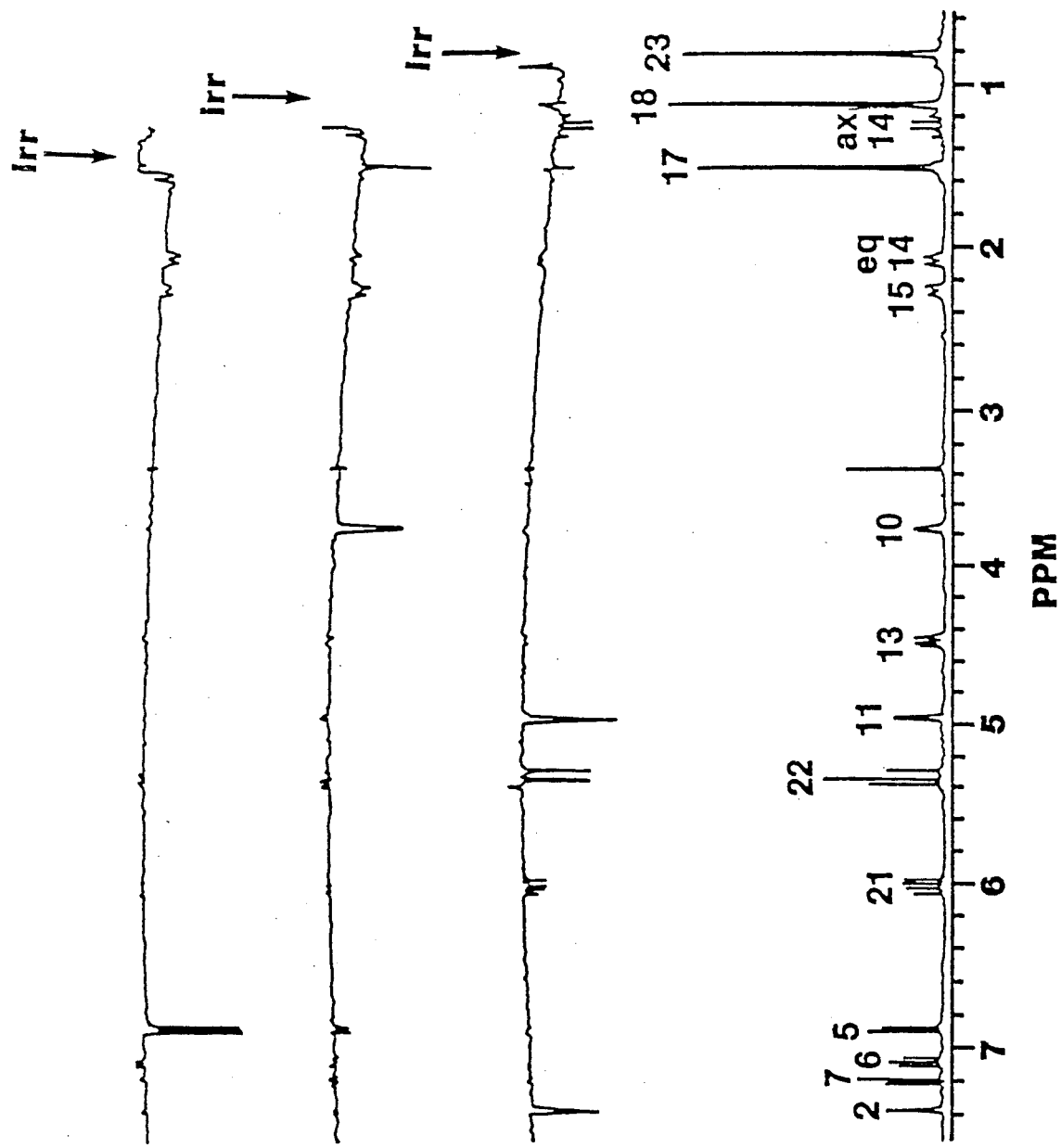

HAPALINDOLES

This invention was made with Government support under Grant No. CHE83-03996 awarded by the National Science Foundation. The Government has certain rights in this invention.

CROSS REFERENCE TO RELATED APPLICATION

This application is a continuation of application Ser. No. 648,114 filed Sept. 7, 1984 which is a continuation-in-part of application Ser. No. 638,847, filed Aug. 8, 1984 both of which are abandoned.

SUMMARY OF THE INVENTION

This invention relates to new alkaloids and to methods of preparing these alkaloids by culturing the blue-green alga (cyanobacterium) *Hapalosiphon fontinalis* ATCC 39694. The new alkaloids, called hapalindoles, are antibacterial and antifungal agents.

DESCRIPTION OF THE DRAWING

The accompanying drawing is a 300 MHz $^1$H nuclear magnetic resonance (NMR) spectrum of hapalindole A in dimethyl sulfoxide-d$_6$. The difference nuclear Overhauser effect (nOe) spectra resulting from irradiation of the C-17, C-18, and C-23 methyl groups are also shown (Positive nOes are down).

DETAILED DESCRIPTION

This invention relates to new antibacterial agents. In particular, this invention provides useful new alkaloids, called hapalindoles A-I, which can be prepared by culturing the blue-green alga *Hapalosiphon fontinalis* ATCC 39694. The new alkaloids of this invention have been assigned the structures shown in formulae 1–9

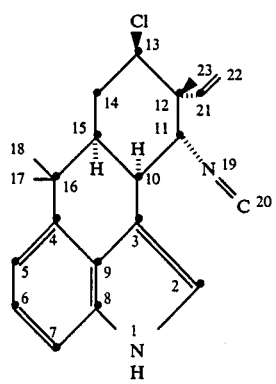

Hapalindole A (1)

-continued

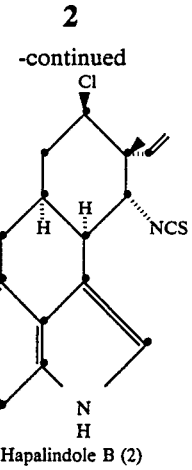

Hapalindole B (2)

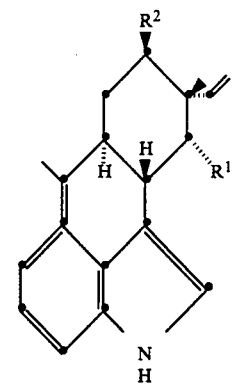

|  | $R^1$ | $R^2$ |
| --- | --- | --- |
| Hapalindole C (3) | NC | H |
| Hapalindole D (4) | NCS | H |
| Hapalindole E (5) | NC | Cl |
| Hapalindole F (6) | NCS | Cl |

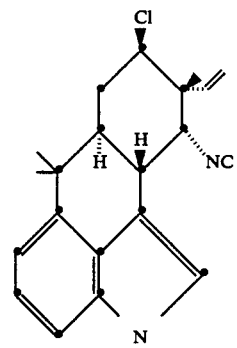

Hapalindole G (7)

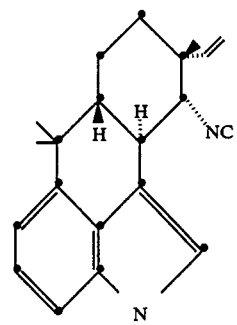

Hapalindole H (8)

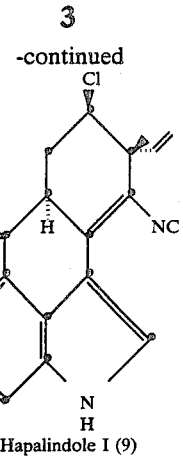

Hapalindole I (9)

The hapalindoles of this invention are produced by cultivating a new strain of the blue-green alga *Hapalosiphon fontinalis* (Ag.) Bornet (Stigonemataceae). This new strain, which was isolated from soil samples collected in the Marshall Islands by repeated subculture on solidified media, was given the strain number V-3-1. It has been deposited and made part of the stock culture collection of The American Type Culture Collection, 12301 Parklawn Drive, Rockville, Md. 20852, from which it is available to the public under the accession number ATCC 39694.

As is the case with other organisms, the characteristics of *Hapalosiphon fontinalis* ATCC 39695 are subject to variation. For example, recombinants, variants or mutants of the ATCC 39694 strain may be obtained by treatment with various known physical and chemical mutagens, such as ultraviolet rays, X-rays, gamma rays, and N-methyl-N'nitro-N-nitrosoguanidine. All natural and induced variants, mutants and recombinants of *Hapalosiphon fontinalis* ATCC 39694 which retain the characteristic of producing a hapalindole compound may be used in this invention.

The hapalindole alkaloids of this invention are prepared by culturing a strain of *Hapalosiphon fontinalis* which produces these compounds under submerged aerobic conditions in a suitable culture medium until substantial antibiotic activity is produced. Other culture techniques, such as surface growth on solidified media, can also be used to produce these compounds. The culture medium used to grow *Hapalosiphon fontinalis* ATCC 39694 can be any one of a number of media. Economy in production, optimal yield, and ease of product isolation are factors to consider when choosing the carbon sources and nitrogen sources to be used. Among the nutrient inorganic salts which can be incorporated in the culture media are the customary soluble salts capable of yielding iron, potassium, sodium, magnesium, calcium, ammonium, chloride, carbonate, phosphate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of the hapalindoles, submerged aerobic cultivation in tanks can be used. Small quantities may be obtained by shake-flask culture. Because of the time lag in antibiotic production commonly associated with inoculation of large tanks with the organism, it is preferable to use a vegetative inoculum. The vegetative inoculum is prepared by inoculating a small volume of culture medium with the spore or akinete-containing form or fragments of the vegetative trichome of the organism to obtain a fresh, actively growing culture of the organism. The vegetative inoculum is then transferred to a larger tank. The medium used for the vegetative inoculum can be the same as that used for larger fermentations, but other media can also be used.

*H. fontinalis* ATCC 39694 can be grown at temperatures between about 20° and about 30° C. The hapalindole compounds are produced at a temperature of about 24° C. and an incident illumination intensity of 330 microEinsteings-$m^{-2}$-$sec^{-1}$. Light intensities somewhat higher or lower can also be used to produce these compounds.

As is customary in aerobic submerged culture processes of this type, $CO_2$ in sterile air is bubbled through the culture medium. For efficient production of the hapalindoles, the precent of $CO_2$ should be about 1% (at 24° C. and one atmosphere of pressure).

Hapalindole production can be followed during the cultivation by testing samples of the broth against organisms known to be sensitive to these antibiotics. One useful assay organism is *Staphylococcus aureus*.

Following their production under submerged aerobic cultivation conditions, the hapalindoles can be recovered from the cultivation medium by methods used in this art. Recovery is generally accomplished by initially filtering the culture medium to separate the algal cells and then freeze drying the separated cells. The freeze fried alga can be be extracted with a suitable solvent such as isopropanol, dichloromethane, or ethyl acetate. The alkaloids can be separated by subjecting this extract to gel filtration and silica-gel chromatography. The alkaloids can be purified by high-performance liquid chromatography (HPLC).

The hapalindoles of this invention inhibit the growth of various pathogenic bacteria, especially gram-positive positive bacteria. Table I summarizes the minimal inhibitory concentrations (MIC's) at which the compounds inhibit certain organisms, as determined by standard agar-dilution assays.

TABLE I

| | In Vitro Antibacterial Activity Of Hapalindoles | | | | | | | |
|---|---|---|---|---|---|---|---|---|
| | MIC (mcg/ml) Compound No. | | | | | | | |
| Organism | 1 | 2 | 3 | 4 | 5 | 6 | 7 | 8 |
| *Staphylococcus aureus* X1.1 | 4 | 2 | 16 | 4 | 4 | 16 | 64 | >64 |
| *Staphylococcus aureus* V41 | 4 | 2 | 16 | 4 | 2 | >64 | 64 | >64 |
| *Staphylococcus aureus* X400 | 4 | 2 | 16 | 8 | 4 | 32 | 64 | >64 |
| *Staphylococcus aureus* S13E | 4 | 2 | 8 | 4 | 2 | 32 | 64 | >64 |
| *Staphylococcus epidermidis* EPI1 | 2 | 2 | 8 | 8 | 2 | 4 | 8 | 32 |

TABLE I-continued

In Vitro Antibacterial Activity Of Hapalindoles

| Organism | MIC (mcg/ml) Compound No. | | | | | | | |
|---|---|---|---|---|---|---|---|---|
| | 1 | 2 | 3 | 4 | 5 | 6 | 7 | 8 |
| *Staphylococcus epidermidis* 222 | 0.06 | 2 | 16 | 4 | 2 | 4 | 16 | 32 |
| *Streptococcus pyogenes* C203 | 2 | 64 | >64 | >64 | >64 | >64 | 16 | 32 |
| *Streptococcus pneumoniae* Park 1 | 16 | 64 | >64 | >64 | >64 | >64 | 16 | 32 |
| *Streptococcus faecium* ATCC 9790 | 16 | 4 | >64 | 8 | 64 | 64 | >64 | >64 |
| Streptococcus sp group D 2041 | 16 | 8 | >64 | 8 | >64 | 16 | >64 | >64 |
| *Haemophilus influenzae* C.L. | 4 | >64 | 16 | >64 | 4 | >64 | 64 | >64 |
| *Haemophilus influenzae* 76 | 4 | >64 | 16 | >64 | 4 | >64 | 64 | >64 |
| *Escherichia coli* N10 | 4 | >64 | >64 | >64 | 16 | >64 | >64 | >64 |
| *Escherichia coli* EC14 | 8 | >64 | >64 | >64 | 16 | >64 | >64 | >64 |
| *Escherichia coli* TEM | 4 | >64 | 64 | >64 | >64 | >64 | >64 | >64 |
| *Klebsiella pneumoniae* X26 | 4 | >64 | >64 | >64 | >64 | >64 | 64 | >64 |
| *Klebsiella pneumoniae* X68 | >64 | >64 | >64 | >64 | >64 | >64 | >64 | >64 |
| *Klebsiella pneumoniae* KAE | >64 | >64 | >64 | >64 | >64 | >64 | >64 | >64 |
| Salmonella sp. X514 | 8 | >64 | >64 | >64 | >64 | >64 | >64 | >64 |
| *Shigella sonnei* N9 | 8 | >64 | >64 | >64 | >64 | >64 | >64 | >64 |
| *Proteus morganii* PR15 | 32 | >64 | >64 | >64 | 32 | >64 | >64 | >64 |
| *Acinetobacter calcoaceticus* AC12 | 2 | >64 | 2 | >64 | >64 | >64 | 16 | 16 |

The hapalindoles of this invention also inhibit the growth of pathogenic fungi. Table II summarizes the MIC's at which the compounds inhibit test organisms, as determined by standard disc-plate assays.

TABLE II

In Vitro Antifungal Activity of Hapalindoles

| Compound | MIC mcg/ml | |
|---|---|---|
| | *Candida albicans* | *Trichophyton mentagrophytes* |
| 1 | 1.25 | 1.25 |
| 2 | >20 | >20 |
| 3 | 0.625 | 0.625 |
| 4 | >20 | >20 |
| 5 | 0.312 | 0.625 |
| 6 | >20 | >20 |
| 7 | 10 | 2.5 |
| 8 | 10 | 1.25 |

EXAMPLE 1

Culture of *Hapalosiphon fontinalis* ATCC 39694

*Hapalosiphon fontinalis* strain V-3-1 (ATCC 39694) was cultured in 25-L glass bottles containing an inorganic medium having the following composition:

| Ingredient | Amount |
|---|---|
| $NaNO_3$ | 200 mg/L |
| $NH_4Cl$ | 10 mg/L |
| $K_2HPO_4.3H_2O$ | 65 mg/L |
| $MgSO_4.7H_2O$ | 50 mg/L |
| $CaCl_2.2H_2O$ | 13 mg/L |
| 3-(N—morpholino)-propanesulfonic acid | 627 mg/L |
| Minor elements solution[a] | 1 mL/L |
| Trace elements solution[b] | 3/25 (0.12) mL/L |

Prior to autoclaving, the pH of the complete medium is adjusted to 7 with sodium hydroxide.

[a]Minor Elements Solution:

| Ingredient | Amount |
|---|---|
| $FeCl_3.6H_2O$ | 0.54 g/L |
| $Na_2EDTA$ | 3.0 g/L |
| $H_3BO_3$ | 0.62 g/L |
| $MnCl_2.4H_2O$ | 1.4 g/L |
| $ZnCl_2$ | 0.10 g/L |
| $CoCl_2.6H_2O$ | 5 mg/L |
| $CuCl_2.2H_2O$ | 34 mcg/L |

[b]Trace Elements Solution:

| Ingredient | Amount (mg/10 L of 0.1 N $H_2SO_4$) |
|---|---|
| $MoO_3$ (85%) | 176.4 |
| $NH_4VO_3$ | 229.6 |
| $Cr_2K_2(SO_4)_4.24H_2O$ | 960.2 |
| $NiSO_4.6H_2O$ | 447.8 |
| $Co(NO_3)_2.6H_2O$ | 493.8 |
| $Na_2WO_4.2H_2O$ | 179.4 |
| $Al_2(SO_4)_3$ | 317.1 |
| $As_2O_3$ | 66.1 |
| $CdCl_2$ | 81.5 |
| $SrSO_4$ | 104.9 |
| $HgCl_2$ | 67.7 |
| $PbCl_2$ | 67.1 |
| LiCl | 305.5 |
| $Rb_2SO_4$ | 78.1 |
| NaBr | 64.4 |
| KI | 65.4 |
| NaF | 110.5 |
| $Na_2SeO_4$ | 119.4 |
| $Be(NO_3)_2.3H_2O$ | 1037.0 |

Cultures were illuminated continuously at an incident intensity of 330 microEinsteins-m$^{-2}$-sec$^{-1}$ from banks of cool-white fluorescent tubes. Cultures were vigorously aerated with 1% $CO_2$ in air and incubated at 24°±1° C. Alga was cultured for 24 days and then was harvested by filtration; yields typically were 0.4–0.5 g dry weight of cells per liter of culture.

EXAMPLE 2

A. Isolation of Hapalindoles

Freeze-dried alga prepared as in Example 1 (360 g) was extracted with 1:1 i-PrOH/$CH_2Cl_2$. The oily extract (15.1 g) was subjected to gel filtration on Sephadex LH-20 with 1:1 i-PrOH/$CH_2Cl_2$ and then to rapid chromatography on silica gel (tlc grade), eluting with hexane, 1:1 hexane/$CH_2Cl_2$, $CH_2Cl_2$, $CH_2Cl_2$/EtOAc, EtOAc, and EtOAC/EtOH. The fraction eluted with 1:1 hexane/$CH_2Cl_2$ was purified by HPLC on Whatman Partisil with 1:1 hexane/$CH_2Cl_2$ to give [after crystallization from $CH_2Cl_2$ and sublimation at 125° (0.1 mm)] 2.1 g (0.58%) of hapalindole A (1).

The remaining hapalindoles were isolated in smaller amounts from the Partisil column. The nine alkaloids were eluted in the following order: 4, 6, 2, 1, 5, 3, 8, 7 and 9.

B. Characteristics of Hapalindole A (1)

Empirical formula: $C_{21}H_{23}N_2Cl$.
mp: 160°–167° (dec).
$[\alpha]_D$: $-78°$ (c 1.2, $CH_2Cl_2$).
UV $\lambda_{max}$(ethanol): 222 nm ($\epsilon$38,000), 280 (7000), 291 (5800)
IR ($CHCl_3$): 2145 cm$^{-1}$.
High resolution EIMS m/z: 338.1595.
$^1$H NMR: see accompanying drawing and Table III.
$^{13}$C NMR: see Table III.

TABLE III
NMR Data for Hapalindole A (1) in CDCl$_3$

| $^{13}C \, \delta^{a,b}$ | Carbon | $^1H \, \delta^c$ |
| --- | --- | --- |
| 157.40 s$^d$ | 20 | |
| 142.99 d | 21 | 6.100 dd |
| 137.52 s | 8 | |
| 133.17 s | 4 | |
| 123.58 s | 9 | |
| 123.21 d | 6 | 7.190 m |
| 118.48 d | 2 | 6.878 t |
| 115.90 t | 22 | 5.346 dd |
| | | 5.236 dd |
| 113.65 d | 5 | 6.969 m |
| 110.14 s | 3 | |
| 108.33 d | 7 | 7.199 m |
| 63.59 d$^d$ | 11 | 4.373 br d |
| 62.99 d | 13 | 4.360 dd |
| 44.39 d | 15 | 2.317 ddd |
| 43.86 s | 12 | |
| 37.76 s | 16 | |
| 36.80 d | 10 | 3.875 br m |
| 31.64 q | 18 | 1.193 s |
| 30.82 t | 14 | 2.142$^e$ dtd |
| | | 1.472$^f$ q |
| 24.07 q | 17 | 1.553 s |
| 18.60 q | 23 | 0.878 s |
| | 1 | 8.085 br |

$J_{H,H}$ (Hz): 1,2 = 2; 1,7 = $\sim$0.5$^g$; 2,6 = $\sim$0.5$^g$; 2,10 = 2; 5,6 = 7.2$^{g,h}$; 5,7 = 0.6$^{g,h}$; 6,7 = 8.2$^{g,h}$; 10,11 = 1.6$^g$; 10,14$_{eq}$ = 1.2; 10,15 = 4.6; 13,14$_{ax}$ = 12.4; 13,14$_{eq}$ = 4.0; 14$_{ax}$,14$_{eq}$ = $-$13.5; 14$_{ax}$,15 = 13.0; 14$_{eq}$,15 = 3.8; trans 21,22 = 17.4; cis 21,22 = 10.9; gem 22,22 = 0.5.

$^a$75 MHz; CDCl$_3$ as internal reference = 76.90.
$^b$$^1$H–$^{13}$C connectivities determined using a phase-cycled 16-step heteronuclear chemical shift correlation map experiment.
$^c$300 MHz; residual CHCl$_3$ as internal reference = 7.25.
$^d$Broad 1:1:1 triplet in proton-noise decoupled spectrum, $J_{13C14C}$$\sim$5 Hz.
$^e$Equatorial.
$^f$Axial.
$^g$Determined in benzene-d$_6$.
$^h$From simulation of ABX spectrum shown by protons on C-5, C-6, and C-7.

C. Characteristics of Hapalindole B (2)

Empirical Formula: $C_{21}H_{23}N_2ClS$.
$[\alpha]_D$: $-194°$ (c 5.1, $CH_2Cl_2$).
IR ($CHCl_3$): 2080, 2160 cm$^{-1}$.
High resolution EIMS m/z: 370.1243.
$^1$H NMR (CDCl$_3$): $\delta$8.064 (br, NH), 7.197 (m, 7.2 and 0.6 Hz, C-5 H), 7.183 (m, 8.2 and 7.2 Hz, C-6 H), 6.961 (m, 8.2 and 0.6 Hz, C-7 H), 6.882 (t, 2.0 Hz, C-2 H), 6.018 (dd, 17.4 and 10.9 Hz, C-21 H), 5.322 (dd, 10.9 and 0.5 Hz, C-22 H cis to C-21 H), 5.123 (dd, 17.4 and 0.5, C-22 H trans to C-21 H), 4,535 (d, 2.3 Hz, C-11 H), 4.319 (dd, 12.6 and 3.9 Hz, C-13 H), 3.867 (br m, C-10 H), 2.220 (ddd, 12.8, 4.6, and 3.6 Hz, C-15 H), 2.149 (dtd, $-$13.3, 3.9, 3.6, and 1.1 Hz, eq H on C-14), 1.555 (s, 3H on C-17), 1,489 (q, $-$13.3, 12.8, and 12.6 Hz, ax H on C-14), 1.198 (s, 3H on C-18), 0.870 (s, 3H on C-23).

Similar (to 1) nOe effects are seen on irradiation of the Me signals at $\delta$0.870, 1.198, and 1.555.
$^{13}$C NMR (CDCl$_3$): $\delta$143.46 (C-21), 137.78 (C-8), 133.33 (C-4), 132.54 (C-20), 123.83 (C-9), 123.39 (C-6), 118.65 (C-2), 115.74 (C-22), 113.84 (C-7), 110.65 (C-3), 108.45 (C-5), 66.91 (C-11), 63.65 (C-13), 46.04 (C-12), 45.23 (C-15), 38.05 (C-16), 37.49 (C-10), 31.89 (C-18), 31.11 (C-14), 24.31 (C-17), 19.23 (C-23).

D. Characteristics of Hapalindole C (3)

Empirical formula: $C_{21}H_{24}N_2$.
mp: 138°–143°.
IR ($CHCl_3$): 2150 cm$^{-1}$.
$^1$H NMR (CDCl$_3$): $\delta$8.115 (br, H on N-1), 7.189 (br d, C-2 H), 7.466 (dm, C-4 H), 7.123 (ddd, C-5 H), 7.185 (ddd, C-6 H), 7.366 (ddd, C-7 H), 3.549 (dd, C-10 H), 3.664 (br m, C-11 H), 2.056 and 1.550 (m, 2H on C-13), 1.83 (m, ax H on C-14), 1.78 (m, eq H on C-14), 2.870 (m, C-15 H), 4.814 (br dq, Z H on C-17), 4.661 (pentuplet, E H on C-17), 1,535 (dd, 3H on C-18), 5.916 (dd, C-21 H), 5.12 (m, E H on C-22), 5.11 (m, Z H on C-22), 1,371 (s, 3H on C-23); H (1,2)=2.5 Hz, (2,10)=0.5, (4,5)=7.7, (4,6)=1.2, (4.7)=0.8, (5,6)=7.1, (5,7)=1.1, (6,7)=8.1, (10,11)=2.8, (10,15)=12.1, (11,13 eq)=1.5, (13,13)=$-$13.9, (13eq,14ax)=3.8, (14,14)=$-$13.9, (14ax,15)=12, (14eq,15)=3.3, (17,17)=2.0, (17Z,18)=0.8, (17E,18)=1.5, (21, 22Z)=17.7, (21,22E)=10.7, (22,22)=0.9.

E. Characteristics of Hapalindole D [4]

Empirical formula: $C_{21}H_{24}N_2S$.
mp: 105°–107°.
$[\alpha]_D$: +239° (c 1.2, $CH_2Cl_2$).
IR ($CHCl_3$): 2180, sh 2130 cm$^{-1}$.
$^1$H NMR (CDCl$_3$): $\delta$8.106 (H on N-1), 7.100, (C-2 H), 7.482 (C-4 H), 7.127 (C-5 H), 7.198 (C-6 H), 7.370 (C-7 H), 3.575 (C-10 H), 3.822 (C-11 H), 1.998 and 1.582 (2H on C-13), 1.84 (ax H on C-14), 1.80 (eq H on C-14), 2.818 (C-15 H), 4.826 (Z H on C-17), 4.666 (E H on C-17), 1.537 (3H on C-18), 5.870 (C-21 H), 5.105 (E H on C-22), 5.095 (Z H on C-22), 1.349 (3H on C-23); coupling constants are essentially the same as above for 3, but signal for H on C-11 does not show coupling to N-19.

F. Characteristics of Hapalindole E [5]

Empirical formula: $C_{21}H_{23}N_2Cl$.
mp: 88°–90°.
$[\alpha]_D$: +25.2° (c 3.1, $CH_2Cl_2$).
IR (KBr): 2140 cm$^{-1}$.
High resolution EIMS m/z: 338.1532.
$^1$H NMR (CDCl$_3$): $\delta$ 8.120 (br, H on N-1), 7.168 (br d, C-2 H), 7.439 (ddt, C-4 H), 7.131 (ddd, C-5 H), 7.197 (ddd, C-6 H), 7.377 (ddd, C-7 H), 3.610 (br dd, C-10 H), 3.811 (br d, C-11 H), 4.459 (dd, C-13 H), 2.248 (ddd, eq H on C-14), 2.151 (dt, ax H on C-14), 3.060 (td, C-15 H), 4.852 (dq, Z H on C-17), 4.717 (pentuplet, E H on C-17), 1.548 (dd, 3 H on C-18), 6.045 (dd, C-21 H), 5.299 (dd, E H on C-22), 5.252 (dd, Z H on C-22), 1.481 (s, 3 H on C-23); J (1,2)=2.2 Hz, (1,10)=0.3, (4,5)=7.7, (4,6)=1.2, (4,7)=0.8, (5,6)=7.1, (5,7)=1.1, (6,7)=8.1, (10,11)=2.9, (10,15)=12.2, (13,14ax)=12.1, (13,14eq)=5.0, (14ax,14eq)=$-$13.7, (14ax,15)=12.2, (14eq,15)=4.3, (17,17)=1.5, (17Z,18)=0.8, (17E,18)=1.5, (21,22E)=10.9, (21,22Z)=17.5, (22,22)=0.3.

$^1$H(irr)$\rightarrow$$^1$H(nOe): $\delta$ 3.610$\rightarrow$7.439(+), 3.811(+); 3.060$\rightarrow$4.852(+), 4.459(+); 1.548$\rightarrow$4.717(+), 3.610(+), 2.151(+); 1.481→5.252(+), 3.811(+), 3.610(+) 2.151(+).

$^{13}$C NMR (CDCl$_3$): δ 123,45 (C-2), 111.74 (C-3), 116.84 (C-4), 119.52 (C-5), 122.05 (C-6), 111.44 (C-7), 135.50 (C-8), 126.23 (C-9), 34.71 (C-10), 67.04 (C-11), 44.54 (C-12), 60.77 (C-13), 38.10 (C-14), 43.90 (C-15), 145.10 (C-16), 113.36 (C-17), 18.55 (C-18), 158.45 (C-20), 141.70 (C-21), 116.06 (C-22), 16.04 (C-23).

G. Characteristics of Hapalindole F (6)

Empirical formula: C$_{21}$H$_{23}$N$_2$ClS.
mp: 176°–179°.
IR (KBr): 2170, 2110 cm$^{-1}$.
$^1$H NMR (CDCl$_3$): δ 8.149 (H on N-1), 7.083 (C-2 H), 7.465 (C-4 H), 7.139 (C-5 H), 7.210 (C-6 H), 7.378 (C-7 H), 3.649 (C-10 H), 4.026 (C-11 H), 4.411 (C-13 H), 2.256 (eq H on C-14), 2.170 (ax H on C-14), 3.017 (C-15 H), 4.866 (Z H on C-17), 4.724 (E H on C-17), 1.550 (3 H on C-18), 5.984 (H on C-21), 5.277 (E H on C-22), 5.233 (Z H on C-22), 1.467 (3H on C-23); coupling constants are essentially the same as those above for 5.

H. Characteristics of Hapalindole G (7)

Empirical formula: C$_{21}$H$_{22}$N$_2$Cl.
mp: >185° C. (dec.)
IR(CHCl$_3$): 2150 cm$^{-1}$.
High resolution EIMS: m/z 338.153
$^1$H NMR (CDCl$_3$): δ 8.044 (br, H on N-1), 7.197 (m, C-7 H), 7.184 (m, C-6 H), 7.035 (m, C-5 H), 6.891 (dd, C-2 H), 6.137 (dd, C-21 H), 5.394 (dd, E H on C-22), 5.342 (dd, Z H on C-22), 4.430 (dd, C-13 H), 4.238 (br d, C-11 H), 3.322 (br dm, C-10 H), 2.407 (ddd, eq H on C-14), 2.105 (ddd, C-15 H), 2.005 (dt, ax H on C-14), 1.520 (s, 3H on pseudo eq C-18), 1.388 (s, 3H on ax C-23), 1.168 (s, 3H on pseudo ax C-17); J(1,2)=2.2 Hz, J(2,10)=1.6, J(5,6)=7.2, J(5,7)=0.6, J(6,7)=8.2, J(10,11)=3.1, J(10,15)=10.4, J(13,14eq)=4.5, J(13,14ax)=11.9, J(14eq,14ax)=−12.5, J(14eq,15)=3.0, J(14ax,15)=11.9, J(21,22Z)=17.4, J(21,22E)=10.9, J(22,22)=0.5.

$^1$H(irr)→$^1$H(nOe): 1.520→7.035(+), 2.407(+), 2.105(+); 1.388→6.137 (small +), 5.342(+), 4.238(+), 3.322(+), 2.005(+); 1.168→7.035 (small +), 3.322(+), 2.005(+).

I. Characteristics of Hapalindole H (8)

Empirical formula: C$_{21}$H$_{24}$N$_2$.
mp: 190°–193°.
[α]$_D$: +152° (c 4.1, CH$_2$Cl$_2$).
IR(KBr): 2150 cm$^{-1}$
EIMS: m/z 304
$^1$H NMR (CDCl$_3$): δ 8.038 (br, H on N-1), 7.621 (dd, C-2 H), 7.020 (m, C-5 H), 7.176 (m, C-6 H), 7.189 (m, C-7 H), 3.167 (td, C-10 H), 3.505 (br dtd), 2.066 (dt. eq H on C-13), 1.380 (td, ax H on C-13) 1.785 (dq, eq H on C-14), 1.657 (qd, ax H on C-14), 1.517 (ddd, C-15 H), 1.449 (s, 3 H on C-17), 1.106 (s, 3 H on C-18), 6.288 (ddd, C-21 H), 5.358 (ddd, E H on C-22), 5.290 (dd, Z H on C-22), 1.278 (s, 3 H on C-23); J(1,2)=2.2 Hz, (2,10)=1.6, (5,6)=7.2, (5,7)=0.6, (6,7)=8.2, (10,11)=10.8, (10,15)=11.0, (11,22 E)=0.4, (13,13)=−13.9, (13ax, 14ax)=13, (13ax,14eq)=3.5, (13eq, 14ax)=3.2, (13eq,14eq)=3.5, (13ax,21)=0.5, (14,14)=−13.2, (14ax,15)=12.0, (14eq,15)=3.5, (21,22E)=11.1, (21,22Z)=17.5, (22,22)=1.1

$^1$H(irr)→$^1$H(nOe): δ 1.449→7.020(+); 1.278→6.288(+), 5.290(+), 3.505(+), 1.106→3.167(+)

$^{13}$C NMR (CDCl$_3$): "118.33 (C-2), 113.03 (C-3), 140.54 (C-4), 112.47 (C-5), 108.07 (C-6), 122.56 (C-7), 133.22 (C-8), 124.88 (C-9), 36.24 (C-10), 67.83 (C-11), 37.25, (C-16), 36.14 (C-13), 20.78 (C-14), 49.73 (C-15), 40.47 (C-12), 24.47 (C-17), 24.75 (C-18), 157.53 (C-20), 138.47 (C-21), 115.83 (C-22), 27.24 (C-23).

J. Characteristics of Hapalindole I (9)

Empirical formula: C$_{21}$H$_{21}$N$_2$Cl.
mp: 180° (dec).
IR (KBr): 2110 cm$^{-1}$.
High resolution EIMS: m/z 336.1366.
$^1$H NMR (CDCl$_3$): δ 8.427 (br, H on N-1), 7.903 (d, C-2 H), 7.061 (m, C-5 H), 7.239 and 7.226 (m, C-6 H and C-7 H), 4.140 (dd, C-13 H), 2.405 (ddd, eq H on C-14), 2.225 (td, ax H on C-14), 2.860 (dd, C-15 H), 1.542 (s, 3 H on C-17), 1.064 (s, 3H on C-18), 5.850 (dd, C-21 H), 5.459 (dd, E H on C-22), 5.358 (dd, Z H on C-22), 1.473 (s, 3 H on C-23); J(1,2)=2.6, (5,6)=7.2, (5,7)=0.6, (6,7)=8.2, (13,14az)=12.9, (13,14eq)=3.6, (14ax,15)=11.6, (14eq,15) 6.2, (14,14)=−13.2, (21,22 E)=10.7, (21,22 Z)=17.3, (22E,22Z)=0.5

$^1$H(irr)→$^1$H(nOe): δ 1.542→7.061(+), 2.860(+). 2.405(+); 1.473→5.850(+), 5.358(+), 2.225(+); 1.064→2.225(+).

We claim:
1. Hapalindole A of the formula:

2. Hapalindole B of the formula

3. A compound of the formula

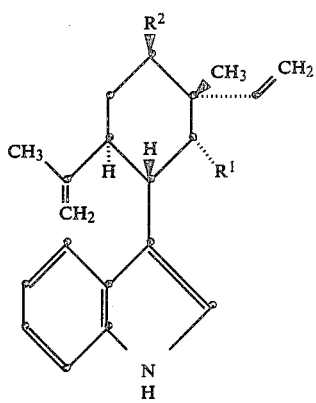
wherein R[1] is —NC or —NCS and R[2] is hydrogen or chlorine.
4. The compound of claim 3 wherein R[1] is —NC and R[2] is hydrogen.
5. The compound of claim 3 wherein R[1] is —NC and R[2] is chlorine.
6. Hapalindole G of the formula
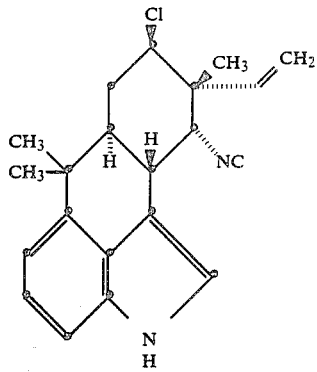
7. Hapalindole H of the formula
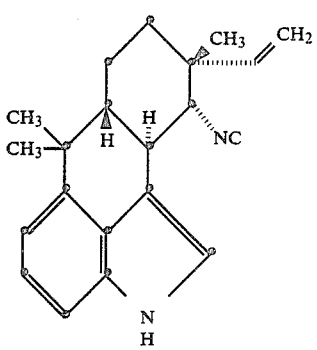
8. Hapalindole I of the formula:
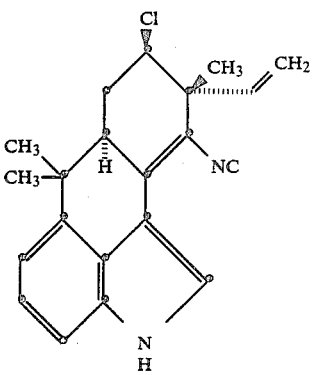
* * * * *